(12) United States Patent
Herry et al.

(10) Patent No.: US 9,877,925 B2
(45) Date of Patent: Jan. 30, 2018

(54) ALCOHOL-RESISTANT ORAL PHARMACEUTICAL FORM

(71) Applicant: ETHYPHARM, Saint-Cloud (FR)

(72) Inventors: Catherine Herry, Saint-Ouen du Tilleul (FR); Laury Trichard, Pony de l'Arche (FR)

(73) Assignee: ETHYPHARM, Saint-Cloud (FR)

( * ) Notice: Subject to any disclaimer, the term of this patent is extended or adjusted under 35 U.S.C. 154(b) by 0 days.

(21) Appl. No.: 14/644,706

(22) Filed: Mar. 11, 2015

(65) Prior Publication Data

US 2015/0250737 A1  Sep. 10, 2015
US 2017/0065531 A9  Mar. 9, 2017

Related U.S. Application Data

(62) Division of application No. 13/697,947, filed as application No. PCT/EP2011/055460 on Apr. 7, 2011, now abandoned.

(30) Foreign Application Priority Data

May 14, 2010 (FR) ..................... 10 53763

(51) Int. Cl.
| | |
|---|---|
| *A61K 9/50* | (2006.01) |
| *A61K 31/485* | (2006.01) |
| *A61K 31/135* | (2006.01) |
| *A61K 31/195* | (2006.01) |
| *A61K 31/554* | (2006.01) |

(52) U.S. Cl.
CPC .......... *A61K 9/5047* (2013.01); *A61K 9/5078* (2013.01); *A61K 31/135* (2013.01); *A61K 31/195* (2013.01); *A61K 31/485* (2013.01); *A61K 31/554* (2013.01)

(58) Field of Classification Search
CPC .. A61K 31/135; A61K 31/195; A61K 31/485; A61K 31/554; A61K 9/5047; A61K 9/5078
See application file for complete search history.

(56) References Cited

U.S. PATENT DOCUMENTS

| | | | |
|---|---|---|---|
| 2005/0020613 A1* | 1/2005 | Boehm ................ | A61K 31/485 514/282 |
| 2007/0264326 A1 | 11/2007 | Guimberteau | |
| 2008/0031946 A1* | 2/2008 | Tchoreloff .......... | A61K 9/2072 424/468 |
| 2008/0063725 A1* | 3/2008 | Guimberteau ....... | A61K 9/2018 424/492 |
| 2009/0041838 A1 | 2/2009 | Guimberteau | |
| 2011/0177138 A1 | 7/2011 | Herry | |

FOREIGN PATENT DOCUMENTS

| | | |
|---|---|---|
| WO | WO 2006/125819 | 11/2006 |
| WO | WO 2008/021394 | 2/2008 |
| WO | WO 2009/036811 | 3/2009 |
| WO | WO 2010/037854 | 4/2010 |

OTHER PUBLICATIONS

International Search Report in Application No. PCT/EP2011/055460, dated Jul. 27, 2011.
Translation of Written Opinion of the ISR PCT/2011/055460.

* cited by examiner

*Primary Examiner* — Michael B. Pallay
(74) *Attorney, Agent, or Firm* — Dinsmore & Shohl LLP

(57) ABSTRACT

A sustained release oral pharmaceutical form suitable for single daily dose administration has a neutral microgranule coated with a mounting layer of active ingredient and pharmaceutically acceptable binder; and a coating layer of a hydrophobic coating polymer of a non-water soluble cellulose derivative, and at least 20% of inert load in relation to dry weight of hydrophobic coating polymer. The pharmaceutical form has improved resistance to rapid release of active ingredient, particularly in the presence of alcohol.

15 Claims, 10 Drawing Sheets

ALCOHOL-RESISTANT ORAL PHARMACEUTICAL FORM

CROSS REFERENCE TO RELATED APPLICATIONS

This Application is a Divisional of U.S. application Ser. No. 13/697,947, filed Nov. 14, 2012, which is a national stage of PCT/EP2011/055460, filed Apr. 7, 2011, which claims priority under U.S.C. §119 to French Application No. 1053763, filed May 14, 2010, the contents of which are incorporated by reference in its entirety herein.

BACKGROUND

The invention relates to a novel oral pharmaceutical form containing microgranules, this form being with the sustained release of at least one active ingredient and with release kinetics enabling notably a single daily dose taken by the patient while preventing this release from accelerating due to the simultaneous consumption of alcohol.

Many sustained-release oral pharmaceutical forms exist on the market. The release of the active ingredient must be controlled according to the therapeutic objective and the pharmacological properties of the active ingredient. Certain active ingredients prove to be highly toxic, even deadly, if the ingested dose exceeds a certain threshold.

It is thus imperative that their "delay" properties are strictly controlled in order to ensure that the rapid release of the active ingredient ("dose dumping") cannot occur, notably when alcohol is consumed at the same time. The consumption of alcohol at the same time as a dose of a drug can indeed alter the pharmaceutical form, which then very rapidly releases all of the active ingredient contained therein. Furthermore, to improve patient comfort, it is desirable to provide a drug that has a pharmacological effect over a long period of time after administration.

For example, this is particularly true for people suffering from severe pain and for whom the pharmacological response must be maintained over a long period with a constant therapeutic level over time.

In order to evaluate the alcohol resistance of pharmaceutical compositions, the United States Food and Drug Administration (FDA) suggests performing in vitro dissolution tests to compare the kinetics obtained in 0.1 N HCl medium (representative of gastric pH) with the kinetics obtained in the same medium substituted with 5%, 20% and 40% (v/v) ethanol. According to Walden et al. (The Effect of Ethanol on the Release of Opioids 30 from Oral Prolonged-Release Preparations, Drug Development and Industrial Pharmacy, 33:10, 1101-1111, 2007), the fact of exposing in vitro a pharmaceutical form over a period of 2 h is regarded as representative of the exposure time of these pharmaceutical forms in vivo.

Patent EP1189602, known from the state of the art, describes sustained release morphine sulfate microgranules. This document proposes microgranules comprised of a neutral carrier coated with an active layer and a sustained release layer containing a copolymer of methacrylic acid and methyl methacrylate ester as well as hydrophobic silica. However, this form of microgranule has the disadvantage of very quickly releasing the active ingredient in the presence of alcohol, which can be harmful or even lethal to the patient.

Patent application WO2010037854, also known from the state of the art, proposes to use a carrier of neutrals that are insoluble or are made insoluble in water or alcohol to avoid an immediate release of the active ingredient induced by the consumption of alcohol. However, this carrier is limited in terms of its resistance to alcohol since the maximum percentage of ethanol in the dissolution medium is 30% and thus this carrier would not resist large volumes of strong alcohols such as whiskey or vodka. Moreover, this patent application does not make it possible to obtain dissolution kinetics compatible with a single daily administration.

Applications WO2009/036812 and WO2010/034342 relate to pH-dependent controlled-release pharmaceutical compositions comprising opioids whose dissolution kinetics are not appreciably affected by the presence of ethanol. More particularly, these pharmaceutical compositions are essentially comprised of a core containing the active substance onto which is coated a layer of a mixture of polymer and a mixture of inert lubricant.

However, the description forces the use of pH-dependent polymers which can induce changes in behavior in man depending on the individual and the conditions under which the drug was taken (notably with or without food).

An essential objective of the present invention is thus to propose an oral pharmaceutical form containing microgranules with sustained release of at least one active ingredient, making it possible to avoid or limit an immediate release of the active ingredient induced by the consumption of alcohol during the administration of this pharmaceutical form. Furthermore, this pharmaceutical form must be easy to produce industrially and at a lower cost.

Definitions in the context of the present description of the invention:

Neutral Carrier

The term "neutral carrier" or "neutral core" or more simply "neutral" means spherical or quasi-spherical inert carriers of a size between 50 μm and 3 mm, preferentially between 100 μm and 1000 μm, such as those generally used in the pharmaceutical industry as a carrier base for active ingredients for the production of microgranules, for example.

Microgranules

The microgranules of the present invention relate to spherical galenic units, comprised in their center of a neutral carrier, covered with at least one layer containing the active ingredient which itself is covered with at least one polymer layer.

Pharmaceutical Form

The term "oral pharmaceutical form" refers to any oral pharmaceutical form that can be prepared from microgranules comprising the active ingredient, notably a suspension, syrup, tablet, gelatin capsule or sachet.

Sustained Release

In the present application, the term "sustained release" will be used to indicate a release profile of the active ingredient that is modified compared to that which the active ingredient alone would have had in an immediate release system as defined by the European Pharmacopoeia (quantity of active ingredient released in 45 minutes at least equal to 75%, Ph. Eur., 6th edition 2.9.3.)

Alcohol

The term "alcohol" refers to ethanol and the terms "alcohol solution" and "alcohol medium" refer to an aqueous ethanol solution.

The goal of the present invention is to provide a novel oral pharmaceutical composition resistant to the immediate release of the dose of active ingredient due to alcohol and notably enabling a single dose daily.

Preferentially, the expression "resistance to the immediate release of the dose of active ingredient due to alcohol" or "resistance to alcohol" means that the percentage of active ingredient released after 2 hours in a 0.1 N HCI acid-alcohol medium containing alcohol and preferably a quantity of ethanol between 4% and 40% (for example 10%, 20%, 30% or 40%) is not greater by more than 15 percentage points (15% in absolute value) than that released in a medium of 0.1 N HCI.

DETAILED DESCRIPTION

A microgranule of the invention comprises from the center toward the periphery;
a neutral carrier,
at least one mounting layer comprising at least one active ingredient and a pharmaceutically acceptable binder,
at least one coating layer comprising:
 a hydrophobic coating polymer selected from non-water soluble cellulose derivatives, and
 at least 20% of an inert load in relation to the dry weight of the hydrophobic coating polymer.

The hydrophobic polymer prevents the immediate release of the active ingredient.

The coating ensures a sustained release of the active ingredient according to release kinetics suited in particular to a single daily dose or two doses per day.

The invention thus relates to sustained release microgranules comprising from the center toward the periphery:
a neutral carrier,
at least one mounting layer comprising at least one active ingredient 5 and a pharmaceutically acceptable binder,
at least one sustained release coating layer comprising:
 a hydrophobic coating polymer selected from non-water soluble cellulose derivatives,
 at least 20% of an inert load in relation to the dry weight of the hydrophobic coating polymer.

The microgranules of the invention are notably able to be administered orally in a single daily dose or in two daily doses.

The microgranules of the invention have a resistance to alcohol according to which the percentage of active ingredient released after 2 hours in a 0.1 N HCI acid-alcohol medium containing alcohol and preferably a quantity of ethanol between 4% and 40% (for example 10%, 20%, 30% or 40%) is not greater by more than 15 percentage points (15% in absolute value) than that released in a medium of 0.1 N HCI.

The invention also relates to the use of an inert load in the coating of sustained release microgranules comprising from the center toward the periphery:
a neutral carrier,
at least one mounting layer comprising at least one active ingredient and a pharmaceutically acceptable binder,
at least one sustained release coating layer comprising a hydrophobic coating polymer selected from non-water soluble cellulose derivatives,
characterised in that the quantity of the inert load in the sustained release coating of the microgranules is at least 20% in relation to the dry weight of the hydrophobic coating polymer,
to confer on said microgranules a resistance to alcohol.

Alcohol resistance means that the percentage of active ingredient released after 2 hours in a 0.1 N HCI acid-alcohol medium containing alcohol and preferably a quantity of ethanol between 4% and 40% (for example 10%, 20%, 30% or 40%) is not greater by more than 15 percentage points (15% in absolute value) than that released in a medium of 0.1 N HCI.

The invention also relates to an oral pharmaceutical form with sustained release of at least one active ingredient, comprising microgranules of the invention.

More particularly, the invention relates to the use of an oral pharmaceutical form of the invention to avoid or limit an immediate release of the active ingredient induced by the consumption of alcohol during the administration of this pharmaceutical form.

The invention also relates to a pharmaceutical form of the invention to be used as a drug administered orally in a single dose once per day, or in two doses per day.

The invention also relates to a method for preparing the microgranules of the invention.

In the context of the present invention, the neutral carrier can be soluble in water or in an alcohol solution but it can also be insoluble in water or in an alcohol solution or can be made insoluble in water or in an alcohol solution by means of a pre-mounting layer.

Suitable neutral carriers that are insoluble in water or in an alcohol solution include carriers containing at least one hydrophobic excipient selected from: cellulose, cellulose derivatives (microcrystalline cellulose), phosphate derivatives (calcium phosphates), silica and silicate derivatives (magnesium silicate, aluminum silicates and mixtures thereof), Carnauba wax, polyvinyl alcohol or any other insoluble carrier.

Suitable neutral carriers that are soluble in water or in an alcohol solution include carriers containing at least one excipient selected from: starch, sucrose, polyols such as mannitol or lactose and mixtures thereof.

The neutral carrier can also be made insoluble in water or in an alcohol solution by covering a neutral with a pre-mounting layer comprising at least one hydrophobic polymer, at least one inert load and optionally a surfactant and/or a plasticizer.

The active ingredients are integrated in the active layer in combination with a pharmaceutically acceptable binder, such as those generally used in the pharmaceutical industry to attach active ingredients on the surface of neutral carriers. Thus, the method for attaching the active layer described in patent EP1200071 can certainly be employed to attach the active layer in the context of the present invention.

Preferably, the active layer of the inventive microgranules is applied by the spraying of a dispersion of active ingredient in a solvent (called the mounting dispersion).

Among pharmaceutically acceptable binders, those used in the invention are preferentially hydrophilic binders and notably cellulose derivatives such as HPMC, in particular Pharmacoat® 603 and Pharmacoat® 606 grades, or hydroxypropyl cellulose or hydroxyethyl cellulose, polyvinylpyrrolidone derivatives, in particular PVP K-30 grade and also polyethylene glycol derivatives, in particular polyethylene glycol with a molecular weight between 600 and 7000, such as PEG4000 and PEG6000 in particular, and mixtures thereof, and vinyl derivatives such as polyvinyl alcohol.

The solvent of the sprayed mounting dispersion must be suited to the active ingredient or mixture of active ingredients employed. Thus, water or organic solvents, including ethanol or hydroalcoholic solutions of various concentrations, for example, can be used to prepare the solution at the base of the active layer.

Preferably, the weight percent of the binder in the active layer in relation to the active ingredient is between 25% and 200% w/w, preferably between 50% and 100% w/w.

A surfactant can be added to the mounting phase to improve the solubility of the active ingredient or to stabilize the mounting suspension.

The surfactant is used in a proportion from 0% to 50%, preferentially from 0% to 20%. Surfactants that can be used include fatty-acid alkaline or alkaline-earth salts, sodium dodecyl sulfate and docusate sodium being preferred; polyoxyethylenated oils, preferably polyoxyethylene hydrogenated castor oil; polyoxyethylene-polyoxypropylene copolymers; polyoxyethylene sorbitan esters; polyoxyethylene castor oil derivatives; stearates, preferably calcium, magnesium, aluminum or zinc stearates; polysorbates; stearyl fumarates, preferably sodium stearyl fumarate; glycerol behenate; benzalkonium chloride; cetyltrimethylammonium bromide; cetyl alcohol and mixtures thereof.

To the degree possible, it is preferable to use solvents that are nontoxic and that can be easily eliminated by evaporation during drying so that no traces of the solvent remain in the microgranules.

The coating that enables controlled release contains a hydrophobic polymer that prevents the immediate release of the active ingredient in a quantity preferentially between 30% and 80%, more preferably between 50% and 80%, of the dry weight of said coating layer.

The coating ratio represents the ratio of the quantity of dry weight constituting the coating that ensures sustained release of the active ingredient to the total weight of the microgranule before coating (in dry weight). The coating ratio is from 0.1% to 70% w/w, preferably from 2% to 50% w/w, and more preferentially still from 10% to 40% w/w. In other words, the ratio between the weight of the dry varnish (=polymer and optional additives in dry weight) constituting the coating that prevents immediate release of the active ingredient and the total weight of the microgranule before coating (in dry weight) is from 0.1% to 70% w/w, preferably from 2% to 50% w/w, and more preferential still from 10% to 40%.

The polymers used to ensure a sustained release of the active ingredient are non-water soluble cellulose derivatives, preferably, selected from the following group of compounds: ethylcellulose (Aquacoat ECD30), cellulose acetate butyrate, cellulose acetate and mixtures thereof.

In a particular embodiment of the invention, the sustained release microgranule coating does not contain poly(meth)acrylate, in particular pH-dependent, such as Eudragit® L100-55 (poly(methacrylic acid, ethyl acrylate)1:1).

In a particular embodiment of the invention, the polymer ensuring the sustained release of the active ingredient consists of one or more non-water soluble cellulose derivatives.

The coating layer also comprises at least 20% of an inert load in relation to the dry weight of the polymer coating.

The term "inert load" refers to an agent that is solid at room temperature, pharmaceutically acceptable, non-water soluble and that reduces the permeability of the pharmaceutical form in which it is incorporated.

Preferably, the inert load is incorporated in the coating in powder form, in particular in a micronized form.

Advantageously, the inert load uniformly distributed in the coating layer is selected from the group comprising notably talc, magnesium stearate, glycerol monostearate, silica and silicate derivatives (magnesium silicate, aluminum silicate), magnesium stearyl fumarate and mixtures thereof.

According to particular embodiments of the invention, the quantity of the inert load in relation to the dry weight of the hydrophobic polymer is greater than 50%, greater than 60%, between 51% and 155%, between 61% and 150%, between 61% and 109%, between 65% and 115%, between 65% and 109%, between 70% and 105%, between 80% and 100%, or between 85% and 95%.

According to a particular embodiment of the invention, the neutral carrier is soluble in water or in an alcohol solution and the quantity of the inert load in relation to the dry weight of the hydrophobic polymer is greater than 30% and less than or equal to 155%, preferably less than 120%.

The surfactant is optionally present in the coating in a proportion from 0% to 30% w/w, preferably from 0% to 20% w/w, and more preferentially still from 5% to 15% of the dry weight of the polymer coating. The surfactant is preferably selected from the group comprising the following compounds: fatty-acid alkaline or alkaline-earth salts, sodium dodecyl sulfate and docusate sodium being preferred; polyoxyethylenated oils, preferably polyoxyethylene hydrogenated castor oil; polyoxyethylene-polyoxypropylene copolymers; polyoxyethylene sorbitan esters; polyoxyethylene castor oil derivatives; stearates, preferably calcium, magnesium, aluminum or zinc stearates; polysorbates; stearyl fumarates, preferably sodium stearyl fumarate; glycerol behenate; benzalkonium chloride; cetyltrimethylammonium bromide; cetyl 10 alcohol and mixtures thereof.

The plasticizer is also optionally present in the coating and can be added to the coating dispersion in a proportion of 0% to 50% w/w, preferably from 2% to 25% w/w, in dry weight of the coating polymer.

The plasticizer is notably selected from the following group of compounds: glycerol and esters thereof, preferably in the following sub-group: medium-chain triglycerides, acetylated glycerides, glyceryl monostearate, glyceryl triacetate, glyceryl tributyrate; phthalates, preferably in the following sub-group: dibutyl phthalate, diethyl phthalate, dimethyl phthalate, dioctyl phthalate; citrates, preferably in the following sub-group: acetyl tributyl citrate, acetyl triethyl citrate, tributyl citrate, triethyl citrate; sebacates, preferably in the following sub-group: diethyl sebacate, dibutyl sebacate; adipates; azelates; benzoates; chlorobutanol; polyethylene glycols; vegetable oils; fumarates, preferably diethyl fumarate; malates, preferably diethyl malate; oxalates, preferably diethyl oxalate; succinates, preferably dibutyl succinate; butyrates; cetyl alcohol esters; malonates, preferably diethyl malonate; castor oil and mixtures thereof.

More preferentially, the plasticizer is selected from the following group of compounds: acetylated monoglycerides, notably Myvacet® 9-45, triethyl citrate (TEC), dibutyl sebacate, triacetin and mixtures thereof.

Active Ingredient

The active layer constituting the microgranules of the invention comprises at least one pharmaceutical active ingredient of any nature.

The microgranules of the present invention can comprise as active ingredient hormones or derivatives thereof, for example, active ingredients that act on the central nervous system, active ingredients that act on the cardiovascular system, antibiotics, antivirals and analgesics.

Active ingredients that act on the central nervous system are preferably selected from antiepileptics, antiparkinsonians, psychostimulants, psychotropics, antidepressants, anxiolytics and antipsychotics, for example.

Active ingredients that act on the cardiovascular system are preferably selected from antihypertensives, antithrombotics, antiaggregants and cholesterol-lowering agents, in particular.

Antibiotics can be selected from beta-lactam antibiotics, cyclines, aminoglycosides, macrolides, quinolones, glycopeptide antibiotics, imidazoles, sulfonamides, antitubercular drugs and anti-leprosy drugs, in particular.

Antivirals can be selected in particular from replication inhibitors or viral multiplication inhibitors.

Analgesics can be selected from non-opiate, weak opiate, mixed opioid, morphine or spasmodic analgesics, notably hydrocodone, hydromorphone, morphine, oxycodone, oxymorphone, tramadol, gabapentin and derivatives thereof.

In a particular embodiment of the invention, the microgranules do not comprise an aversive agent, such as rimonabant hydrochloride. The term "aversive agent" refers to an agent that causes an unpleasant physiological or psychological reaction, notably in combination with alcohol or with a psychoactive substance such as *cannabis*.

In another particular embodiment of the invention, the microgranules do not comprise metformin or acyclovir.

Method for Preparing Microgranules

The present invention further relates to a method for preparing the microgranules described above comprising the following steps:
- introduction of spherical neutral carriers that are soluble, insoluble or rendered insoluble in a fluid bed reactor, for example,
- spraying on these spherical neutral carriers of at least one active ingredient in solution or in suspension in an organic and/or aqueous solvent supplemented with at least one water soluble or non-water soluble polymer (binder),
- spraying of a coating suspension comprising at least one hydrophobic polymer and an inert load on the coated particles obtained in the preceding step,
- eventually, drying of the medicinal microgranules thus obtained.

Preparation of the Mounting Dispersion

The mounting step of the active layer of the present invention makes it possible to obtain microgranules whose content in active is both precise and uniform.

The mounting dispersion is the dispersion in which the active ingredients will be dissolved or suspended (dispersed) and which will be sprayed on the surface of the microgranules. This dispersion also contains a dissolved conventional binder.

Mounting of the Active Layer

The active ingredient is applied to the granules in a conventional way by spraying, in a fluid bed reactor or perforated turbine, for example. Generally, this process rests on the simultaneous spraying through a nozzle of the active ingredients and optionally a binder which are dissolved or dispersed in the mounting solution, which guarantees for this step of the method a perfect homogeneity of content. The time necessary for mounting is highly variable and depends on the quantity of active ingredient to be sprayed and its solubility in the mounting solution. Generally it is between 1 hour and 48 hours.

At the conclusion of the mounting step, the microgranules are dried in a fluid bed reactor or perforated turbine and then screened.

Microgranule Coating

The coating polymer is applied to the preceding microgranules in a conventional way by spraying, in a fluid bed reactor or perforated turbine, for example. Generally, this method rests on the simultaneous spraying through a nozzle of the coating polymers, an inert load, and optionally a surfactant and/or a plasticizer which are dissolved or dispersed in a suitable solvent.

An organic solution of polymer can be used for the coating: in this case, the use of a plasticizer is not strictly necessary.

If the excipient is water, an aqueous dispersion of polymer is used. The process then consists of the spraying of the dispersion, drying in the same apparatus and, if necessary, a step of curing the coating film which renders it homogeneous and uniform. Curing can take place in a fluid bed reactor, perforated turbine or oven, for example.

The time necessary for coating is highly variable and depends on the quantity of polymer to be sprayed. At the conclusion of the coating step, the microgranules are dried in a fluid bed reactor and then screened.

Pre-mounting Layer

According to another aspect of the invention and as described above, each microgranule can comprise at least one pre-mounting layer, located between the neutral carrier and the mounting layer, in order to make the neutral carrier insoluble.

Thus, the neutral carrier made insoluble is obtained by covering a neutral with a pre-mounting layer comprising at least one hydrophobic polymer, at least one inert load and optionally a surfactant and/or a plasticizer.

The hydrophobic polymers, inert loads, plasticizers and surfactants are identical to those described above.

The hydrophobic polymer present in the pre-mounting layer will be between 40% and 100%, preferably between 50% and 80%, of the dry weight of the pre-mounting layer.

The inert load can be present in a quantity greater than 50%, greater than 60%, between 51% and 155%, between 61% and 150%, between 61% and 109%, between 65% and 115%, between 65% and 109%, between 70% and 105%, between 80% and 100%, or between 85% and 95% of the dry weight of the hydrophobic polymer.

If the neutral carrier is soluble in water or in an alcohol solution, the quantity of the inert load in relation to the dry weight of the hydrophobic polymer can be greater than 30% and less than or equal to 155%, preferably less than 120%.

The plasticizer contained in the pre-mounting layer can be added in a proportion of 0% to 50% w/w, preferably, from 2% to 25% w/w, in dry weight of the hydrophobic polymer.

A surfactant can also be added to the pre-mounting layer in a proportion of 0% to 30% w/w, preferably from 0% to 20% w/w, and more preferentially still from 5% to 15% of the dry weight of the hydrophobic polymer.

The hydrophobic polymer is applied to the neutrals in a conventional way by spraying, in a fluid bed reactor or perforated turbine, for example. Generally, this method rests on the simultaneous spraying through a nozzle of the hydrophobic polymers, an inert load, and optionally a plasticizer and/or a surfactant which are dissolved or dispersed in a suitable solvent.

An organic solution of polymer can be used to apply the pre-mounting layer, in this case, the use of a plasticizer is not strictly necessary.

If the excipient is water, an aqueous dispersion of polymer is used. The process then consists of the spraying of the dispersion, drying in the same apparatus and, if necessary, a step of curing the coating film which renders it homogeneous and uniform. Curing can take place in a fluid bed reactor, perforated turbine or oven, for example.

Dissolution and Dosage Tests

Generally, the dosage and dissolution conditions of the inventive microgranules are those prescribed by the various Pharmacopoeias, in particular European, American and Japanese.

Thus, to determine the release kinetics of the various systems studied, a conventional temperature-controlled paddle or basket dissolution apparatus can be used. The medicinal units are introduced into each flask and samples are taken periodically to determine the quantity of active ingredient released over time. Samples can be taken manually or automatically and analyses can be carried out directly with a UV/visible spectrophotometer or after HPLC (high-performance liquid chromatography) separation coupled with UV/visible detection, for example.

EXAMPLES

Example 1

Alcohol-resistant sustained release morphine sulfate microgranules (15% coating ratio, expressed in dry weight of the coating polymer in relation to the weight of the microgranules before coating. 50% inert load factor in relation to the dry weight of the hydrophobic coating polymer)

a) Preparation of Sustained Release Morphine Sulfate Microgranules

The active ingredient used is morphine sulfate. The neutral cores used are sugar spheres (NPPHARM SP neutrals). The size of these carriers is roughly 400 µm to 500 µm. The binder used is hydroxypropylmethylcellulose (HPMC 603). It is solubilized in water and then the morphine sulfate is added to this aqueous solution, constituting the mounting solution. The mounting solution is sprayed in a fluid bed reactor (Glatt), as is the coating and pre-mounting suspension.

The qualitative and quantitative compositions of the morphine sulfate microgranules are summarized in the following table.

| Microgranules (15% coating ratio) | | Quantities (g) |
|---|---|---|
| PRE-MOUNTING | SP neutrals | 223.53 |
| | Ethylcellulose | 170.97 |
| | Eq. dry weight | 51.29 |
| | Triethyl citrate | 12.88 |
| | Talc Pharma | 25.56 |
| MOUNTING | Morphine sulfate | 313.30 |
| | HPMC 603 | 109.64 |
| COATING | Ethylcellulose | 367.43 |
| | Eq. dry weight | 110.23 |
| | Triethyl citrate | 26.48 |
| | Talc Pharma | 54.95 |
| Total content | | % |
| SP neutrals | | 24.1 |
| Morphine sulfate | | 33.8 |
| HPMC 603 | | 11.8 |
| Ethylcellulose | | 17.4 |
| Triethyl citrate | | 4.2 |
| Talc Pharma | | 8.7 | b) Microgranule Dosing and Dissolution

In vitro release tests of the active ingredient are carried out in a revolving-paddle dissolution apparatus (European Pharmacopeia, Sotax AT7, IDIS software). The analysis is carried out with a UV/visible spectrophotometer at wavelengths of 285 and 310 nm (Kontron Instruments spectrophotometer, UVIKON 922). The samples are stirred constantly in flasks each containing 500 ml of dissolution medium and the temperature is kept constant at 37° C. (±0.5° C.). The dissolution media used are comprised either of 0.1 N HCl or of a 0.1 N HCl/absolute ethanol mixture with an absolute ethanol concentration of 10%, 20% or 40% (v/v). The rotation speed of the paddles is set at 100 turns/min. Samples are taken continuously over 24 h in each flask of the apparatus. For each flask, the microgranule test sample is equivalent to 120 mg of PA.

c) Profiles Obtained in 0.1 N HCl and Mixtures of 0.1 N HCl/Absolute Ethanol Concentrated at 10%, 20% and 40% (v/v)

Figure 1:
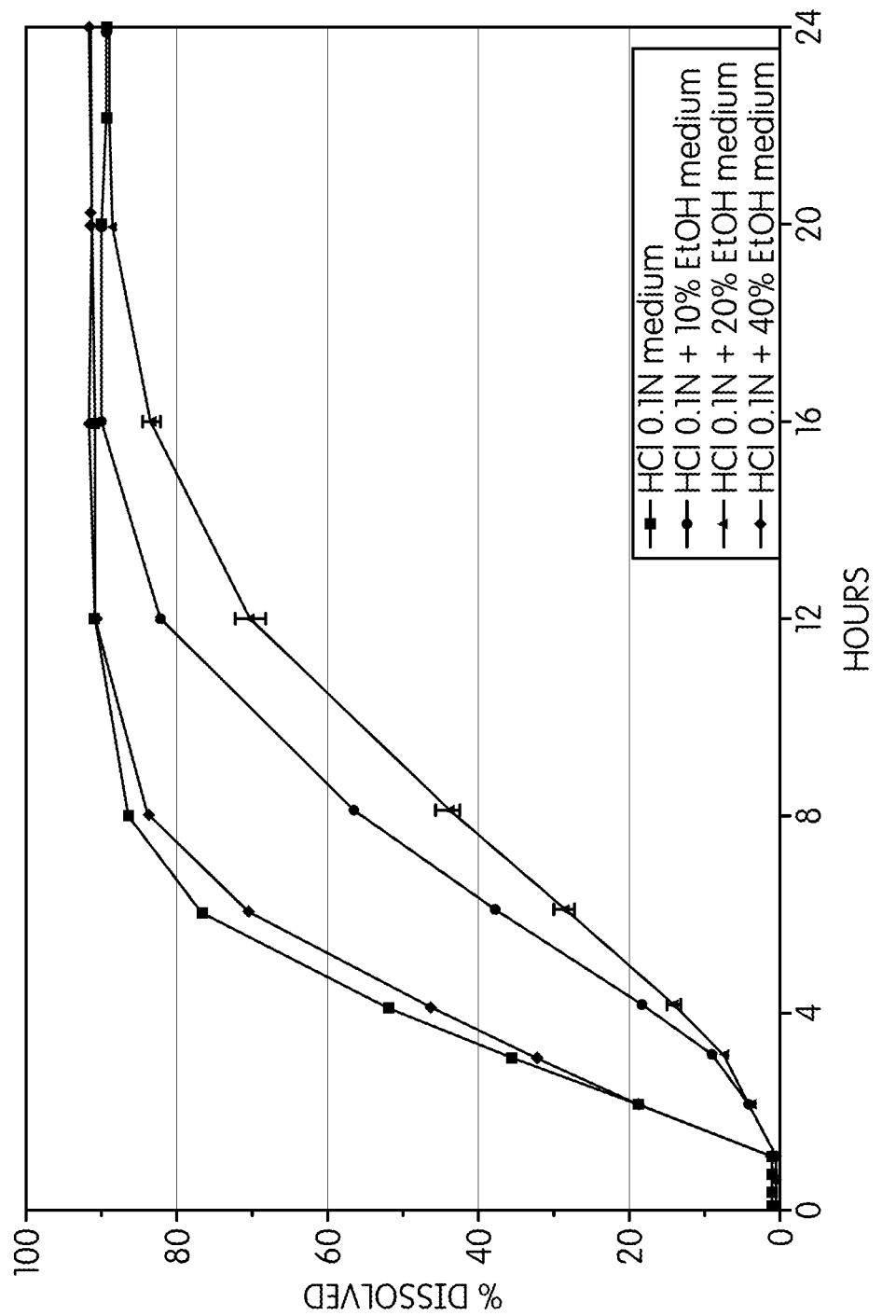
FIG. 1: Dissolution profiles of microgranules containing morphine sulfate and coated with ethylcellulose, triethyl citrate and talc in various media (15% coating ratio, 50% inert load ratio).

The dissolution profiles obtained in 0.1 N HCl and in the mixtures of 0.1 N HCl/absolute ethanol concentrated at 10%, 20% and 40% (v/v) in absolute ethanol for the microgranules having a 15% coating ratio are indicated in FIG. 1.

FIG. 1 shows that the microgranules indeed have a sustained release in the media having an ethanol concentration of 0, 10%, 20% and 40% (v/v).

The difference in the percentages of morphine sulfate released in the acid-alcohol media or the 0.1 N HCl at 2 hours are less than 15% for the three ethanol concentrations, which demonstrates that these microgranules are alcohol resistant.

Example 2

Alcohol-resistant sustained release morphine sulfate microgranules (20% coating ratio, expressed in dry weight of the coating polymer in relation to the weight of the microgranules before coating, 50% inert load factor in relation to the dry weight of the hydrophobic coating polymer)

According to one variant of Example 1, the alcohol resistant morphine sulfate microgranules can be obtained by means of a 20% coating ratio. The methods for preparing, dosing and dissolving the microgranules remain identical to Example 1, except for their quantitative composition summarized in the following table.

| Microgranules (20% coating ratio) | | Quantities (g) |
|---|---|---|
| PRE-MOUNTING | SP neutrals | 223.53 |
| | Ethylcellulose | 170.97 |
| | Eq. dry weight | 51.29 |
| | Triethyl citrate | 12.88 |
| | Talc Pharma | 25.56 |
| MOUNTING | Morphine sulfate | 313.30 |
| | HPMC 603 | 109.64 |
| COATING | Ethylcellulose | 489.9 |
| | Eq. dry weight | 146.97 |
| | Triethyl citrate | 35.3 |
| | Talc Pharma | 73.6 |
| Total content | | % |
| | SP neutrals | 22.5 |
| | Morphine sulfate | 31.6 |
| | HPMC 603 | 11.0 |
| | Ethylcellulose | 20.0 |
| | Triethyl citrate | 4.9 |
| | Talc Pharma | 10.0 |

Figure 2:
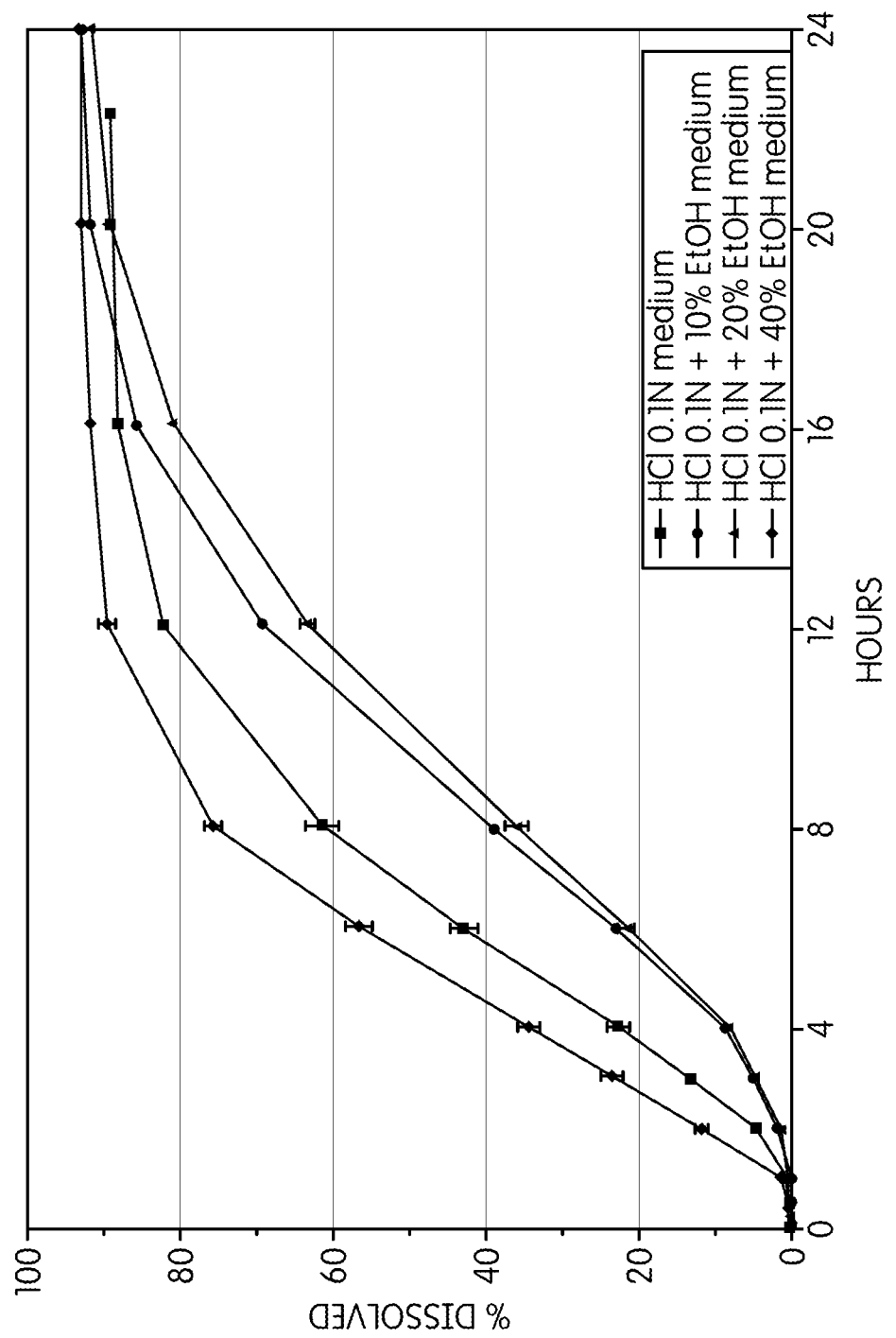
FIG. 2: Dissolution profiles of microgranules containing morphine sulfate and coated with ethylcellulose, triethyl citrate and talc in various media (20% coating ratio, 50% inert load ratio).

The dissolution profiles obtained in 0.1 N HCl and in the mixture of 0.1 N HCl/absolute ethanol concentrated at 10%, 20% and 40% (v/v) in absolute ethanol for the microgranules having a 20% coating ratio are indicated in FIG. 2. The maximum difference in the percentages of active ingredient released after 2 hours in 0.1 N HCl in relation to the acid-alcohol media is 7.1%, or less than 15%, which demonstrates that these microgranules are alcohol resistant.

Example 3

Alcohol-resistant sustained release morphine sulfate microgranules (20% coating ratio, expressed in dry weight of the coating polymer in relation to the weight of the microgranules before coating, 25% inert load factor in relation to the dry weight of the hydrophobic coating polymer)

According to one variant of Examples 1 and 2, the alcohol resistant morphine sulfate microgranules are obtained by decreasing the quantity of the inert load in the coating. The methods for preparing, dosing and dissolving the microgranules remain identical to Example 1, except for their quantitative composition summarized in the following table.

| Microgranules (20% coating ratio) | | Quantities (g) |
|---|---|---|
| PRE-MOUNTING | SP neutrals | 242.90 |
| | Ethylcellulose | 185.80 |
| | Eq. thy weight | 55.74 |
| | Triethyl citrate | 13.99 |
| | Talc Pharma | 27.77 |
| MOUNTING | Morphine sulfate | 340.45 |
| | HPMC 603 | 119.14 |
| COATING | Ethylcellulose | 535.87 |
| | Eq. dry weight | 160.76 |
| | Triethyl citrate | 38.40 |
| | Talc Pharma | 40.13 |
| Total content | | % |
| | SP neutrals | 23.4 |
| | Morphine sulfate | 32.8 |
| | HPMC 603 | 11.5 |
| | Ethylcellulose | 20.8 |
| | Triethyl citrate | 5.0 |
| | Talc Pharma | 6.5 |

Figure 3:
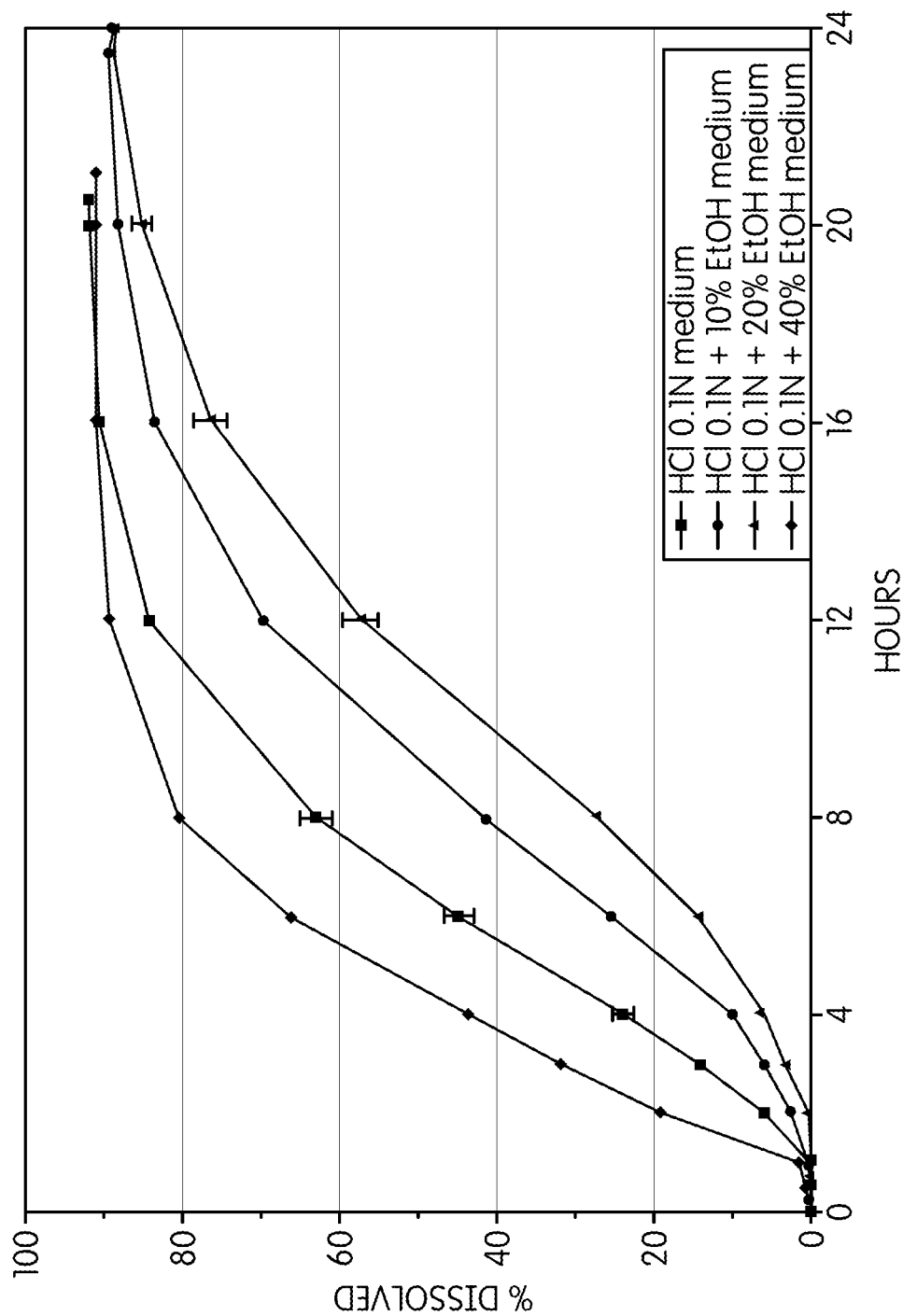
FIG. 3: Dissolution profiles of microgranules containing morphine sulfate and coated with ethylcellulose, triethyl citrate and talc in various media (20% coating ratio, 25% inert load ratio).

The dissolution profiles obtained in 0.1 N HCl and in the mixture of 0.1 N HCl/absolute ethanol concentrated at 10%, 20% and 40% (v/v) in absolute ethanol for the microgranules having a 20% coating ratio are indicated in FIG. 3. The maximum difference in the percentages of active ingredient released after 2 hours in 0.1 N HCl in relation to the acid-alcohol media is 13.5%, which demonstrates that these microgranules are alcohol resistant.

Example 4

Alcohol-resistant sustained release morphine sulfate microgranules (15% coating ratio, expressed in dry weight of the coating polymer in relation to the weight of the microgranules before coating, 50% inert load factor in relation to the dry weight of the hydrophobic coating polymer) lacking a pre-mounting layer According to one variant of Examples 1 and 2, the alcohol resistant morphine sulfate microgranules do not have a pre-mounting layer. The methods for preparing, dosing and dissolving the microgranules remain identical to Example 1, except for the size of the sugar neutrals used (Suglets #30, NPPHARM, 400-600 μm size) and their quantitative composition summarized in the following table.

| Microgranules (15% coating ratio) | | Quantities (g) |
|---|---|---|
| MOUNTING | Neutrals # 30 | 479.89 |
| | Morphine sulfate | 236.98 |
| | HPMC 603 | 83.13 |
| COATING | Ethylcellulose | 400.00 |
| | Eq. oily weight | 120.0 |
| | Triethyl citrate | 28.80 |
| | Talc Pharma | 60.00 |
| Total content | | % |
| | Neutrals # 30 | 47.6 |
| | Morphine sulfate | 23.5 |
| | HPMC 603 | 8.2 |
| | Ethylcellulose | 11.9 |
| | Triethyl citrate | 2.9 |
| | Talc Pharma | 5.9 |

Figure 4:
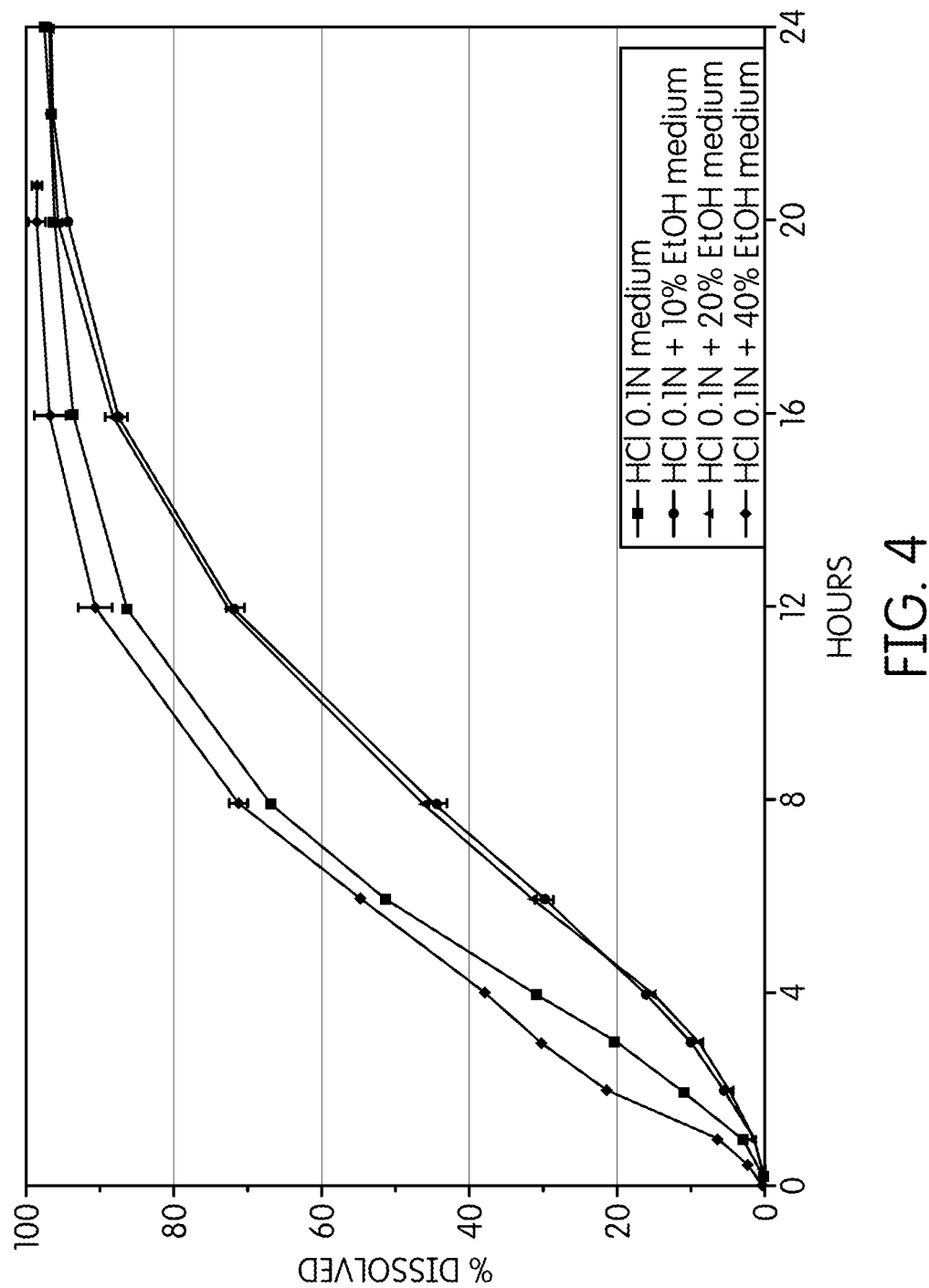
FIG. 4: Dissolution profiles of microgranules containing morphine sulfate and coated with ethylcellulose, triethyl citrate and talc (15% coating ratio, 50% inert load ratio) in various media, the microgranules not comprising a pre-mounting layer.

The dissolution profiles obtained in 0.1 N HCl and in the mixture of 0.1 N 5 HCl/absolute ethanol concentrated at 10%, 20% and 40% (v/v) in absolute ethanol for the microgranules lacking a pre-mounting layer and having a 15% coating ratio are indicated in FIG. 4. The difference in the percentages of active ingredient released after 2 hours in 0.1 N HCl in relation to the acid-alcohol media is 10.5%, or less than 15%, which demonstrates that these microgranules are alcohol resistant.

FIG. 4 shows that the microgranules lacking a pre-mounting layer also exhibit sustained release in the media with an ethanol concentration of 0%, 10%, 20% and 40% (v/v).

Example 5

Alcohol-resistant sustained release morphine sulfate microgranules (15% coating ratio, expressed in dry weight of the coating polymer in relation to the weight of the microgranules before coating, 90% inert load factor in relation to the dry weight of the hydrophobic coating polymer) lacking a pre-mounting layer According to one variant of Example 4, the alcohol resistant morphine sulfate microgranules are obtained by increasing the quantity of the inert load in the coating. The methods for preparing, dosing and dissolving the microgranules remain identical to Example 1, except for the size of the sugar neutrals used (Suglets #30, NPPHARM, 400-600 μm) and their quantitative composition summarized in the following table.

| Microgranules (15% coating ratio) | | Quantities (g) |
| --- | --- | --- |
| MOUNTING | Neutrals # 30 | 479.89 |
| | Morphine sulfate | 236.98 |
| | HPMC 603 | 83.13 |
| COATING | Ethylcellulose | 400.00 |
| | Eq. dry weight | 120.00 |
| | Triethyl citrate | 29.00 |
| | Talc Pharma | 108.00 |
| Total content | | % |
| Neutrals # 30 | | 45.4 |
| Morphine sulfate | | 22.4 |
| HPMC 603 | | 7.9 |
| Ethylcellulose | | 11.4 |
| Triethyl citrate | | 2.7 |
| Talc Pharma | | 10.2 |

Figure 5:
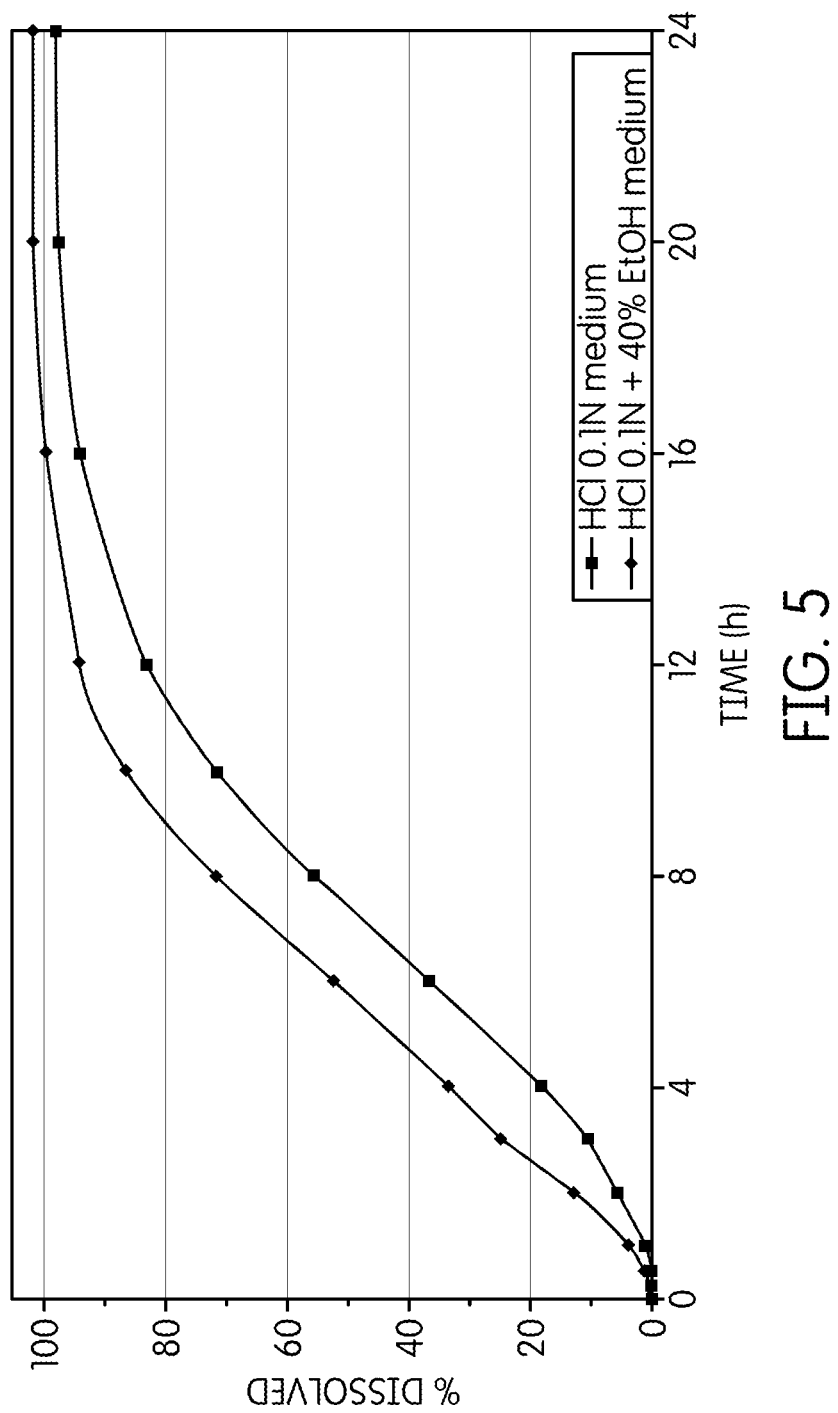
FIG. 5: Dissolution profiles of microgranules containing morphine sulfate and coated with ethylcellulose, triethyl citrate and talc (15% coating ratio, 90% inert load factor) in various media, the microgranules not comprising a pre-mounting layer.

The dissolution profiles obtained in 0.1 N HCl and in the mixture of 0.1 N HCl/absolute ethanol concentrated at 40% (v/v) in absolute ethanol for the microgranules lacking a pre-mounting layer, having a 15% coating ratio and a load factor of 90% are indicated in FIG. 5. The difference in the percentages of active ingredient released after 2 hours in 0.1 N HCl in relation to the acid-alcohol media is 7.7%, or less than 15%, which demonstrates that these microgranules are alcohol resistant.

Example 6

Alcohol-resistant sustained release morphine sulfate microgranules (15% coating ratio, expressed in dry weight of the coating polymer in relation to the weight of the microgranules before coating, 120% inert load factor in relation to the dry weight of the hydrophobic coating polymer) lacking a pre-mounting layer According to one variant of Examples 4 and 5, the alcohol resistant morphine sulfate microgranules are obtained by increasing the quantity of the inert load in the coating. The methods for preparing, dosing and dissolving the microgranules remain identical to Example 1, except for the size of the sugar neutrals used (Suglets #30, NPPHARM, 400-600 μm) and their quantitative composition summarized in the following table.

| Microgranules (15% coating ratio) | | Quantities (g) |
| --- | --- | --- |
| MOUNTING | Neutrals # 30 | 479.89 |
| | Morphine sulfate | 236.98 |
| | HPMC603 | 83.13 |
| COATING | Ethylcellulose | 400.00 |
| | Eq. dry weight | 20.00 |
| | Triethyl citrate | 29.00 |
| | Talc Pharma | 144.00 |
| Total content | | % |
| Neutrals # 30 | | 43.9 |
| Morphine sulfate | | 21.7 |
| HPMC603 | | 7.6 |
| Ethylcellulose | | 11.0 |
| Triethyl citrate | | 2.7 |
| Neutrals #30 | | 42.5 |
| Morphine sulfate | | 21.0 |
| HPMC 603 | | 7.4 |
| Ethylcellulose | | 10.6 |
| Triethyl citrate | | 2.6 |
| Talc Pharma | | 15.9 |

Figure 7:
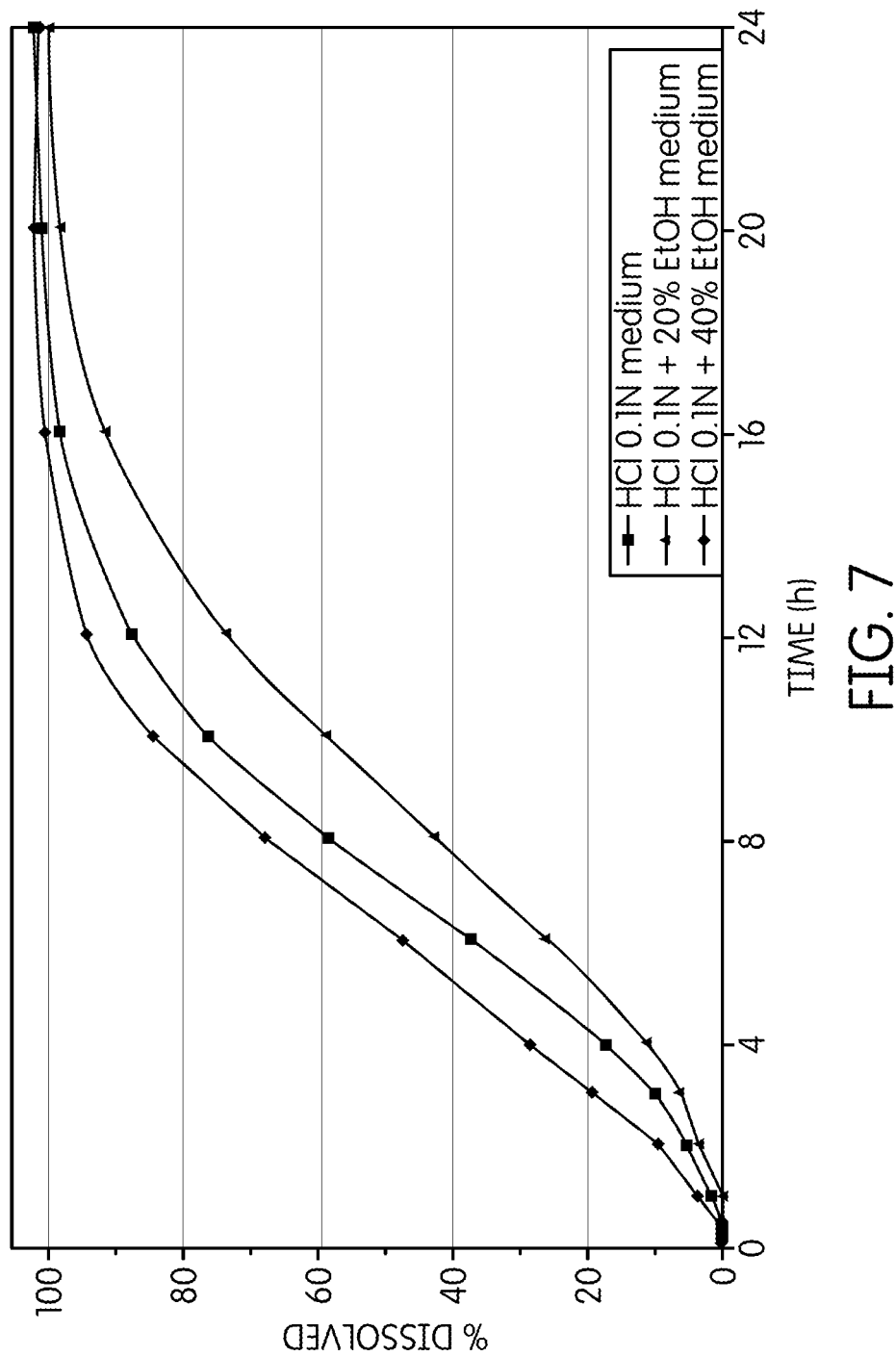
FIG. 7: Dissolution profiles of microgranules containing morphine sulfate and coated with ethylcellulose, triethyl citrate and talc (15% coating ratio, 150% inert load factor) in various media, the microgranules not comprising a pre-mounting layer.
Figure 8:
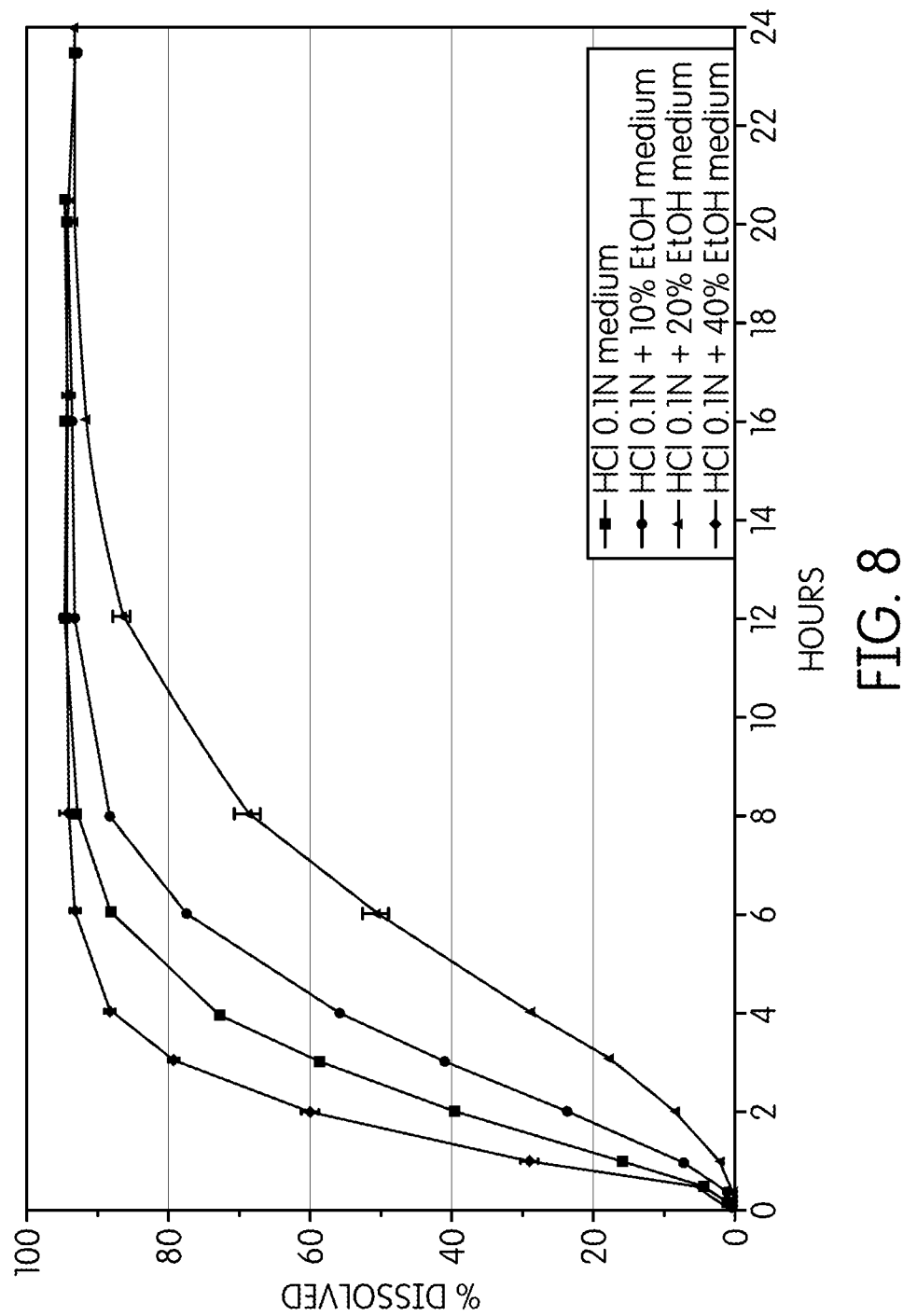
FIG. 8: Dissolution profiles of microgranules comprising morphine sulfate and coated with ethylcellulose and triethyl citrate (10% coating ratio) in various media, the coating layer not containing talc.

The dissolution profiles obtained in 0.1 N HCl and in the mixture of 0.1 N HCl/absolute ethanol concentrated at 40% (v/v) in absolute ethanol for the microgranules lacking a pre-mounting layer, having a 15% coating ratio and a 150% load factor are indicated in FIG. 7. The difference in the percentages of active ingredient released after 2 hours in 0.1 N HCl in relation to the acid-alcohol media is 4.7%, or less than 15%, which demonstrates that these microgranules are alcohol resistant.

Counterexample 8

Sustained release morphine sulfate microgranules (10% coating ratio, expressed in dry weight of the coating polymer in relation to the weight of the microgranules before coating) not containing talc in the coating layer According to one variant, the morphine sulfate microgranules do not contain talc in the coating layer.

The methods for preparing, dosing and dissolving the microgranules remain identical to Example 1, except for their quantitative composition summarized in the following table.

| Microgranules (10% coating ratio) | | Quantities (g) |
| --- | --- | --- |
| PRE-MOUNTING | SP neutrals | 243.15 |
| | Ethylcellulose | 185.80 |
| | Eq. dry weight | 55.59 |
| | Triethyl citrate | 13.89 |
| | Talc Pharma | 27.78 |
| | Talc Pharma | 13.2 |

Figure 6:
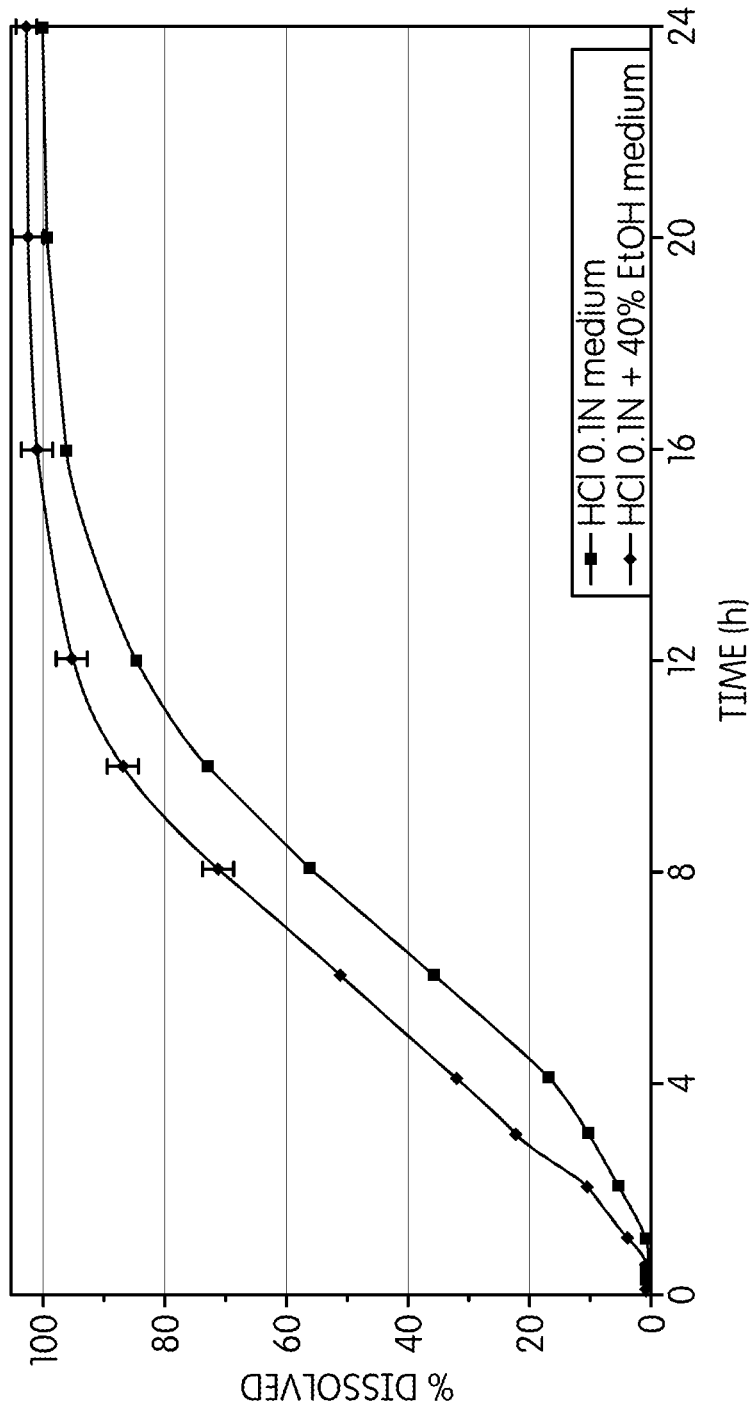
FIG. 6: Dissolution profiles of microgranules containing morphine sulfate and coated with ethylcellulose, triethyl citrate and talc (15% coating ratio, 120% inert load factor) in various media, the microgranules not comprising a pre-mounting layer.

The dissolution profiles obtained in 0.1 N HCl and in the mixture of 0.1 N HCl/absolute ethanol concentrated at 40% (v/v) in absolute ethanol for the microgranules lacking a pre-mounting layer, having a 15% coating ratio and a 120% load factor are indicated in FIG. 6. The difference in the percentages of active ingredient released after 2 hours in 0.1 N HCl in relation to the acid-alcohol media is 5.3%, or less than 15%, which demonstrates that these microgranules are alcohol resistant.

Example 7

Alcohol-resistant sustained release morphine sulfate microgranules (15% coating ratio, expressed in dry weight of the coating polymer in relation to the weight of the microgranules before coating, 150% inert load factor in relation to the dry weight of the hydrophobic coating polymer) lacking a pre-mounting layer According to one variant of Examples 4 to 6, the alcohol resistant 13.2 morphine sulfate microgranules are obtained by increasing the quantity of inert load in the coating. The methods for preparing, dosing and dissolving the microgranules remain identical to Example 1, except for the size of the sugar neutrals used (Suglets #30, NPPHARM, 400-600 μm) and their quantitative composition summarized in the following table.

| Microgranules (15% coating ratio) | | Quantities (g) |
|---|---|---|
| MOUNTING | Neutrals # 30 | 479.89 |
|  | Morphine sulfate | 236.98 |
|  | HPMC 603 | 83.13 |
| COATING | Ethylcellulose | 400.00 |
|  | Eq. dry weight | 120.00 |
|  | Triethyl citrate | 29.00 |
|  | Talc Pharma | 180.00 |
| MOUNTING | Morphine sulfate | 340.43 |
|  | HPMC 603 | 119.15 |
| COATING | Ethylcellulose | 266.80 |
|  | Eq. thy weight | 80.04 |
|  | Triethyl citrate | 19.20 |
|  | Talc Pharma | 0.00 |
| Total content | | % |
| SP neutrals | | 27.04 |
| Morphine sulfate | | 37.86 |
| HPMC 603 | | 13.25 |
| Ethylcellulose | | 15.08 |
| Triethyl citrate | | 3.68 |
| Talc Pharma | | 3.09 |

The dissolution profiles obtained in 0.1 N HCl and in the mixture of 0.1 N HCl/absolute ethanol concentrated at 10%, 20% and 40% (v/v) in absolute ethanol for the microgranules not containing talc in the coating layer and having a 10% coating ratio are indicated in Figures. The difference in the percentages of active ingredient released after 2 hours in 0.1 N HCl in relation to 0.1 N HCl medium supplemented with 40% ethanol is 20.9%, which is greater than 15%. Moreover, the release profile obtained in the alcohol-free medium is unacceptable in terms of single dose daily for the patient.

Counterexample 9

Alcohol-resistant sustained release morphine sulfate microgranules (15% coating ratio, expressed in dry weight of the coating polymer in relation to the weight of the microgranules before coating) not containing talc in the coating layer According to one variant, the alcohol resistant morphine sulfate microgranules do not contain talc in the coating layer.

The methods for preparing, dosing and dissolving the microgranules remain identical to Example 1, except for their quantitative composition summarized in the following table.

| Microgranules (15% coating ratio) | | Quantities (g) |
|---|---|---|
| PRE-MOUNTING | SP neutrals | 243.15 |
|  | Ethylcellulose | 185.80 |
|  | Eq. dry weight | 55.59 |
|  | Triethyl citrate | 13.89 |
|  | Talc Pharma | 27.78 |
| MOUNTING | Morphine sulfate | 340.43 |
|  | HPMC603 | 119.15 |
| COATING | Ethylcellulose | 400.60 |
|  | Eq. dry weight | 120.18 |
|  | Triethyl citrate | 28.90 |
|  | Talc Pharma | 0.00 |
| Total content | | % |
| SP neutrals | | 25.6 |
| Morphine sulfate | | 35.9 |
| HPMC603 | | 12.6 |
| Ethylcellulose | | 18.5 |
| Triethyl citrate | | 4.5 |
| Talc Pharma | | 2.9 |

Figure 9:
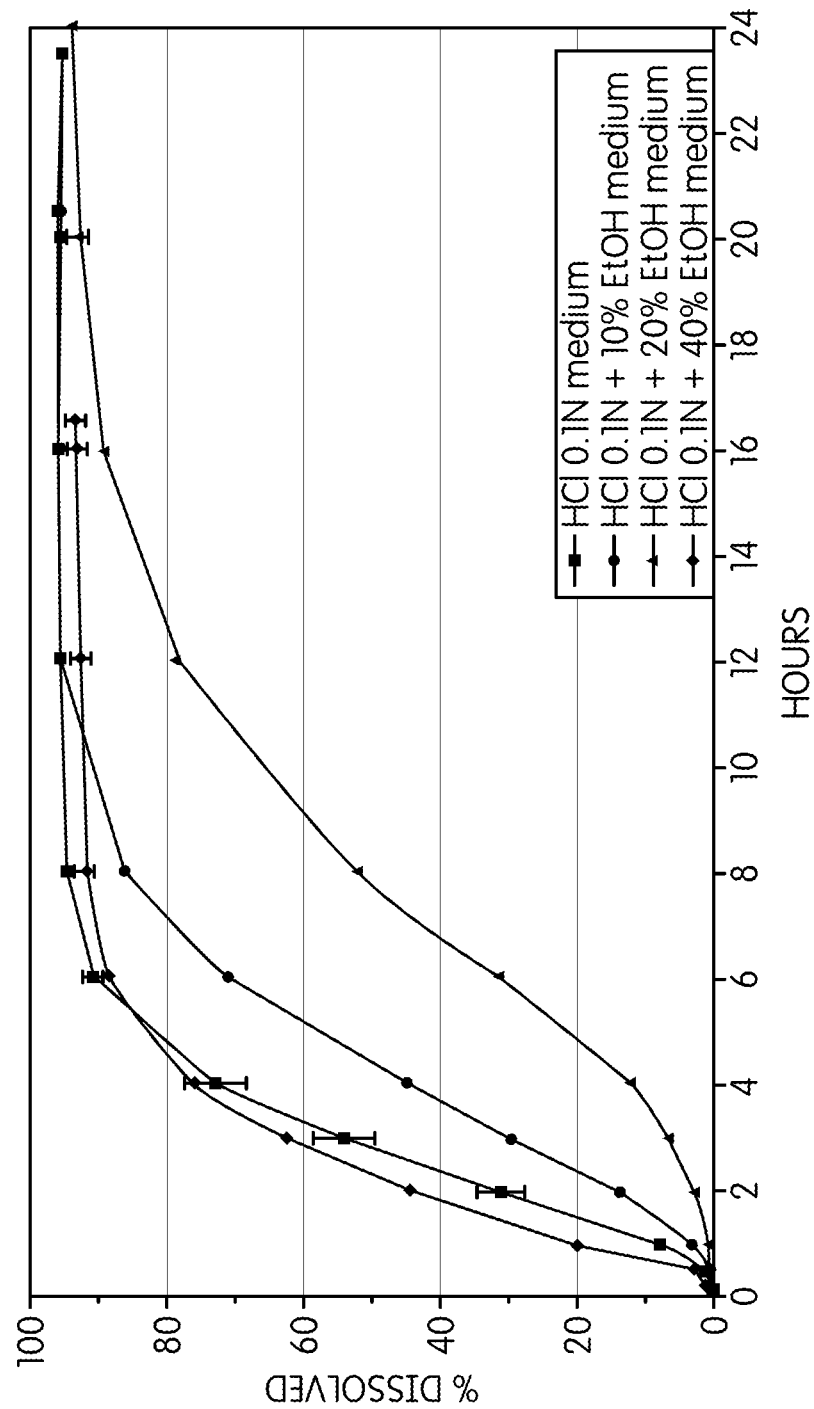
FIG. 9: Dissolution profiles of microgranules comprising morphine sulfate and coated with ethylcellulose and triethyl citrate (15% coating ratio) in various media, the coating layer not containing talc.

The dissolution profiles obtained in 0.1 N HCl and in the mixture of 0.1 N HCl/absolute ethanol concentrated at 10%, 20% and 40% (v/v) in absolute ethanol for the microgranules not containing talc in the coating layer and 10 having a 15% coating ratio are indicated in FIG. 9. The maximum difference in the percentages of active ingredient released after 2 hours in 0.1 N HCl in relation to the acid-alcohol media is 13.0%, or less than 15%, which demonstrates that these microgranules are alcohol resistant. On the other hand, the release profile obtained in the alcohol-free medium free is unacceptable in terms of a single dose daily for the patient, even by increasing the coating ratio from 10% to 15%.

Counterexample 10

Sustained release morphine sulfate microgranules (15% coating ratio, expressed in dry weight of the coating polymer in relation to the weight of the microgranules before coating) containing talc outside of the coating layer According to one variant of Examples 4 to 7, the morphine sulfate microgranules contain talc outside of the coating layer. The methods for preparing, dosing and dissolving the microgranules remain identical to Example 1, except for the size of the sugar neutrals used (Suglets #30, NPPHARM, 400-600 μm) and their quantitative composition summarized in the following table.

| Microgranules (15% coating ratio) | | Quantities (g) |
|---|---|---|
| MOUNTING | Neutrals # 30 | 479.89 |
|  | Morphine sulfate | 236.98 |
|  | HPMC 603 | 83.13 |
| COATING | Ethylcellulose | 400.00 |
|  | Eq. thy weight | 120.00 |
|  | Triethyl citrate | 29.00 |
|  | Talc Pharma | 0.00 |
| OVER-COATING | HPMC 603 | 203.00 |
|  | Talc Pharma | 203.00 |
| Total content | | % |
| Neutrals # 30 | | 35.4 |
| Morphine sulfate | | 17.5 |
| HPMC 603 | | 21.1 |
| Ethylcellulose | | 8.9 |
| Triethyl citrate | | 2.1 |
| Talc Pharma | | 14.9 |

Figure 10:
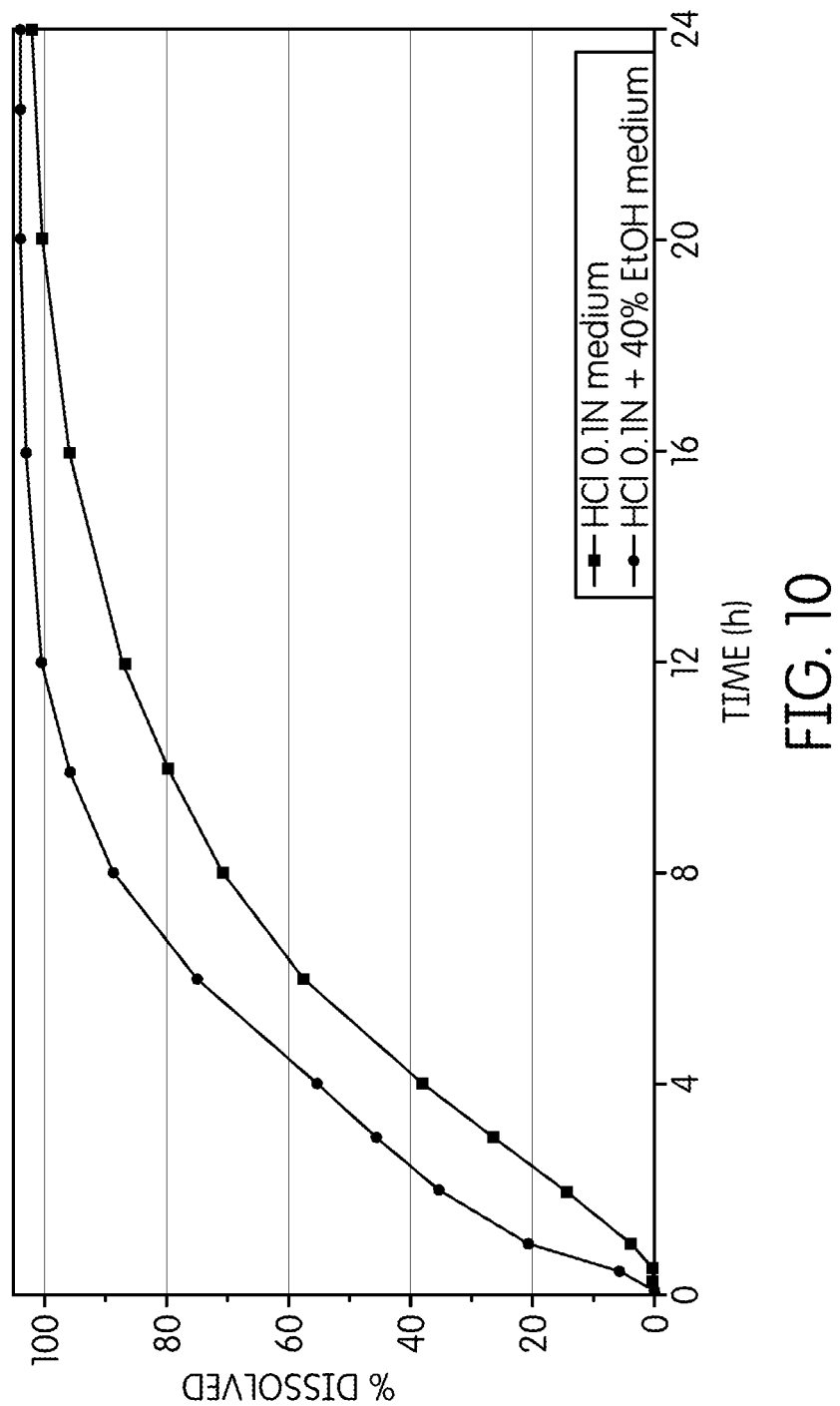
FIG. 10: Dissolution profiles of morphine sulfate microgranules coated with ethylcellulose and triethyl citrate (15% coating ratio) in various media, the microgranules not comprising a pre-mounting layer and containing talc outside of the coating layer.

The dissolution profiles obtained in 0.1 N HCl and in the mixture of 0.1 N HCl/absolute ethanol concentrated at 40% (v/v) in absolute ethanol for the microgranules lacking a pre-mounting layer, having a 15% coating ratio and containing talc outside of the coating layer are indicated in FIG. 10. The difference in the percentages of active ingredient released after 2 hours in 0.1 N HCI in relation to the acid-alcohol media is 21.1%, or greater than 15%, which demonstrates that these microgranules are not alcohol resistant.

Counterexample 11

Sustained release diltiazem microgranules (20% coating ratio, expressed in dry weight of the coating polymer in relation to the weight of the microgranules before coating) not containing talc in the coating layer The methods for preparing, dosing and dissolving the microgranules are identical to Example 1, except for their centesimal composition summarized in the following table:

| Composition | % |
| --- | --- |
| Mounting: | |
| Cellulose neutral carriers | 64.7 |
| Diltiazem HCl | 16.2 |
| PVP K30 | 2.0 |
| Coating: | |
| Ethylcellulose | 13.4 |
| Triethyl citrate | 3.2 |
| Aerosil ® R972 | 0.5 |

The difference in the percentages of active ingredient released after 2 hours in 0.1 N HCI in relation to the acid-alcohol media (mixture of 0.1 N HCI/absolute ethanol concentrated at 10%, 20% and 40% (v/v) in absolute ethanol) is indicated in the following table:

| | 10% ethanol | 20% ethanol | 40% ethanol |
| --- | --- | --- | --- |
| Difference at 2 hours (0-X% of ethanol | −20.2% | 10.8% | 53.3% |
| Alcohol resistance (if difference <15%) | Yes | Yes | No |

The invention claimed is:

1. A method for avoiding or limiting immediate release of an active ingredient induced by the consumption of alcohol during the administration of a once a day sustained release pharmaceutical formulation, said method comprising the consumption of alcohol during the administration of the pharmaceutical formulation, said pharmaceutical formulation comprising granules which comprise, from the center toward the periphery:
   a neutral carrier,
   at least one mounting layer comprising an active ingredient and a pharmaceutically acceptable binder,
   a sustained-release coating layer comprising:
      a hydrophobic coating polymer selected from non-water soluble cellulose derivatives, and
      at least 20% of talk in relation to the dry weight of the hydrophobic coating polymer.

2. The method of claim 1, wherein the hydrophobic coating polymer is selected from the group consisting of ethylcellulose, cellulose acetate butyrate, cellulose acetate and mixtures thereof.

3. The method of claim 1, wherein the quantity of the hydrophobic coating polymer is from 30% to 80% of the dry weight of said coating layer.

4. The method of claim 1, wherein the quantity of the hydrophobic coating polymer is from 50% to 80% of the dry weight of the coating layer.

5. The method of claim 1, wherein the pharmaceutically acceptable binder is selected from the group consisting of cellulose derivatives, polyvinylpyrrolidone derivatives, polyethylene glycol derivatives, vinyl derivatives and mixtures thereof.

6. The method of claim 5, wherein the cellulose derivatives are selected from the group consisting of hydroxypropylmethylcellulos, hydroxypropylcellulose, and hydroxyethyl cellulose; and wherein the vinyl derivative is polyvinyl alcohol.

7. The method of claim 1, further comprising a plasticizer in the coating layer.

8. The method of claim 1, further comprising a surfactant in the coating layer.

9. The method of claim 1, wherein the active ingredient is selected from the group consisting of hormones, active ingredients that act on the central nervous system, active ingredients that act on the cardiovascular system, antibiotics, antivirals and analgesics.

10. The method of claim 7, wherein the active ingredient is selected from the group consisting of non-opiate, weak opiate, mixed opioid, morphine and spasmodic analgesics.

11. The method of claim 7, wherein the active ingredient is selected from the group consisting of morphine and derivatives thereof.

12. The method of claim 7, wherein the active ingredient is morphine sulfate.

13. The method of claim 1, wherein the granules comprise at least one pre-mounting layer between the neutral carrier and the mounting layer, said pre-mounting layer comprising at least one hydrophobic polymer, at least 50% of an inert load in relation to the dry weight of the hydrophobic polymer, and optionally a plasticizer and/or a surfactant.

14. The method of claim 7, wherein the plasticizer is selected from the group consisting of: acetylated glycerides, glyceryl monostearate, glyceryl triacetate, glyceryl tributyrate, phthalates, dibutyl phthalate, diethyl phthalate, dimethyl phthalate, dioctyl phthalate, citrates, acetyl tributyl citrate, acetyl triethyl citrate, tributyl citrate, triethyl citrate, sebacates, diethyl sebacate, dibutyl sebacate, adipates, azelates, benzoates, chlorobutanols, polyethylene glycols, plant oils, fumarates, diethyl fumarate, malates, diethyl malate, oxalates, diethyl oxalate, succinate, dibutyl succinate, butyrates, cetyl alcohol esters, malonates, diethyl malonate, castor oil and mixtures thereof.

15. The method of claim 9, wherein said analgesics are selected from the group consisting of hydrocodone, hydromorphone, morphine, oxycodone, oxymorphone, tramadol, gabapentin, and derivatives thereof.

* * * * *